(12) United States Patent
Schindler et al.

(10) Patent No.: US 7,345,766 B2
(45) Date of Patent: Mar. 18, 2008

(54) MEASURING CHAMBER FOR PHOTO-ACOUSTICAL SENSORS

(75) Inventors: Wolfgang Schindler, Graz (AT); Klaus-Christoph Harms, Thal/Graz (AT); Franz Knopf, Graz (AT); Harald Grantner, Graz (AT)

(73) Assignee: AVL List GmbH, Graz (AT)

( * ) Notice: Subject to any disclaimer, the term of this patent is extended or adjusted under 35 U.S.C. 154(b) by 370 days.

(21) Appl. No.: 11/018,241

(22) Filed: Dec. 22, 2004

(65) Prior Publication Data

US 2005/0160800 A1    Jul. 28, 2005

(30) Foreign Application Priority Data

Jan. 28, 2004    (AT) .............................. GM52/2004

(51) Int. Cl.
*G01N 21/00*    (2006.01)
(52) U.S. Cl. ..................... 356/440; 356/437; 73/24.02
(58) Field of Classification Search ................ 356/432, 356/437, 440, 438, 439
See application file for complete search history.

(56) References Cited

U.S. PATENT DOCUMENTS

| | | | |
|---|---|---|---|
| 4,412,445 A * | 11/1983 | Spellicy ..................... 73/24.02 |
| 4,457,162 A * | 7/1984 | Rush et al. ................. 73/24.01 |
| 5,069,551 A | 12/1991 | Brown | |
| 5,146,283 A * | 9/1992 | Parnoff et al. .............. 356/246 |
| 5,285,677 A * | 2/1994 | Oehler ....................... 73/24.01 |
| 6,594,016 B1 * | 7/2003 | Te Lintel Hekkert et al. ... 356/437 |

* cited by examiner

*Primary Examiner*—Gregory J. Toatley, Jr.
*Assistant Examiner*—Juan D Valentin, II
(74) *Attorney, Agent, or Firm*—Dykema Gossett PLLC

(57) ABSTRACT

A measuring chamber for photo-acoustical sensors for the continuous measurement of radiation-absorbing substances, in particular of radiation-absorbing particles, in gaseous samples includes at least one entry and at least one exit for the samples, a tube section with microphone that allows for the flow-through of the sample in longitudinal direction, and at least one entry and exit point for a laser beam that is aligned with the tube section, and whereby these entry and exit points are both arranged at a distance from the measuring tube by at least one chamber with a cross-sectional area that is expanded relative to the tube section. To prevent soiling of the windows at the points of entry of the radiation into the cell and to slow down the deposition of the particles of the measured aerosol, whereby long-term, high-sensitivity operation of the measuring cell is possible, two entries (2, 3) are envisioned at two ends of the tube section (31) that are opposite relative to each other and at least one exit (4) that is arranged at a location which is centered between the entries (2, 3).

8 Claims, 3 Drawing Sheets

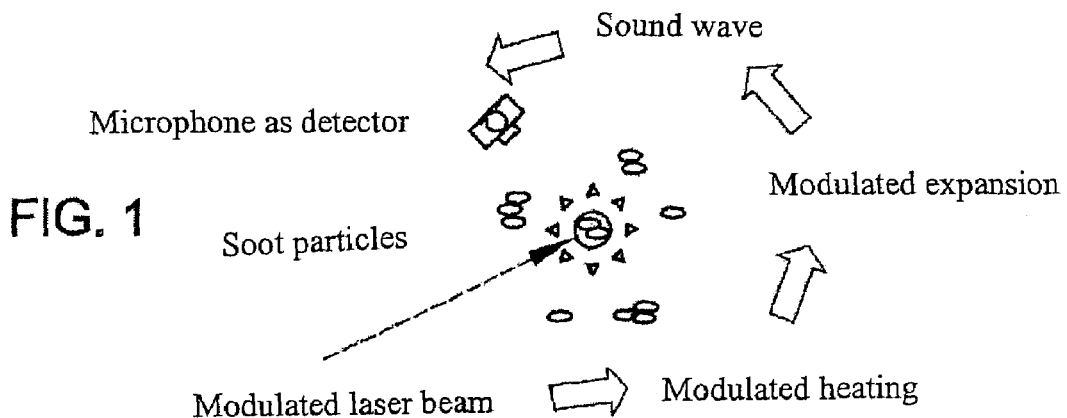
FIG. 1
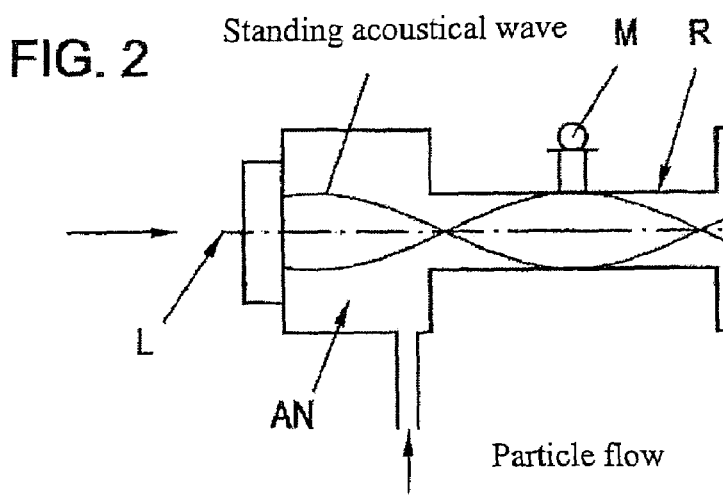
FIG. 2
FIG. 3
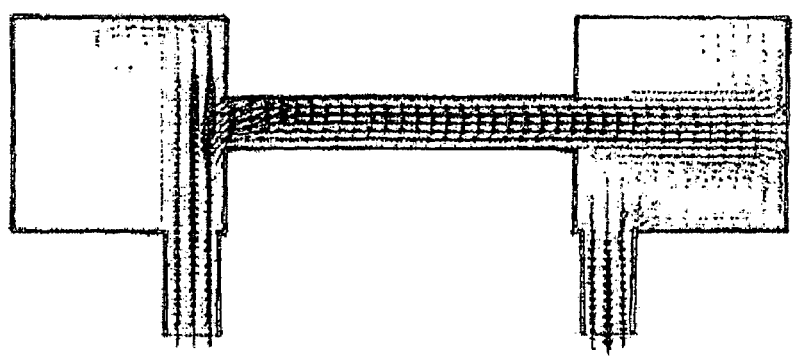

FIG: 6
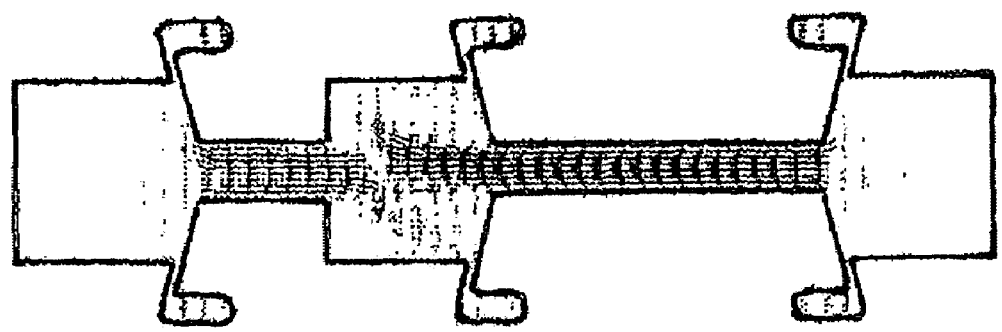

MEASURING CHAMBER FOR PHOTO-ACOUSTICAL SENSORS

BACKGROUND OF THE INVENTION

The invention relates to a measuring chamber for photo-acoustical sensors for the continuous measurement of radiation-absorbing substances, in particular of radiation-absorbing particles, in gaseous samples comprising at least one entry and at least one exit for the samples, a tube section with microphone that allows for the flow-through of the sample in longitudinal direction and with at least one entry and one exit point for the laser beam aligned with the tube section, and whereby said entry and exit points are arranged at a distance relative to the measuring tube respectively by way of at least one chamber with a cross-sectional area that is expanded relative to the tube section.

Photo-acoustics is a very sensitive measuring technique in order to determine, for example, trace gas or aerosol concentrations in a carrier gas. In the-photo-acoustical measuring process a solid, liquid or gaseous sample containing at least one (possibly frequency-selective) radiation-absorbing substance is irradiated with intensity modulated electromagnetic radiation; frequently this is visible or infrared light. Since the substance absorbs the radiation, the substance becomes heated and the heat is given off to the environment during the pauses with low radiative intensity. This results in a periodic heating and cooling of the irradiated volume, which in turn leads to periodic pressure fluctuations propagating in the form of sound waves that can be detected with the use of sensitive microphones. The method is depicted schematically in FIG. 1.

Resonant cells are used to increase the sensitivity by harmonizing the period and/or the frequency of the modulated irradiation with the characteristic frequency of the measuring cell. For a time-resolved measurement of substances in gases the carrier gas must flow through the cell. A simple cell with longitudinal resonance is, for example, described by Krämer and Niessner in the German utility model no. 200 17 795.8 and by Beck, Niessner and Haisch in Anal. Bioanal. Chem. 375 (2003), p. 1136 et seq. This cell is represented schematically in FIG. 2. It is comprised of a tube R the length of which determines the resonance frequency and the diameter of which is considerably smaller than its length. The areas AN with expanded diameter on both ends of the resonance tube R are referred to a "notch" filters. The change in diameter can be viewed as a "fixed end" for the acoustic pressure wave and therefore generates a node of the pressure wave and (A pressure node corresponds to a maximum of the particle velocity). The length of the entire measuring cell amounts to approximately one wavelength lambda of the sound wave, with the following equation indicating the connection of the wavelength lambda relative to the resonance frequency:

Lambda=sound velocity/resonance frequency.

A disadvantage of the shown measuring cell is its susceptibility to soiling of the windows through which the intermittent radiation L enters and exits. This is in particular a grave problem if the photo-acoustic cell is used for measuring aerosols, e.g. soot particles from combustion engines or in general substances from the environment. Flow calculations have shown that, for example, the gas entering on the left of the resonant cell forms vortexes causing a flow toward the window already in the left "notch filter", whereby some particles of the measured aerosol become deposited at the window location resulting in a parasitic effect. After the measured gas passes through the resonant cell, it flows directly toward the opposite window, whereby once again some particles of the measured aerosol are deposited also causing a parasitic effect. The parasitic effect results from the fact that the deposits on the windows also absorb radiation and generate sound waves that superimpose on the measuring signal in the form of interference. An exact measurement, in particular for low concentrations of the measured aerosol, is thereby prevented. The result of a finite element calculation of the flow in this cell is shown in FIG. 3; whereby direction and velocity of the flow are characterized in the figure by the direction and length of vectors.

The usual method for keeping the optical windows in a flow-through apparatus clean, such as in opacimeters provides to rinse the windows with a flow of particle-free air thereby preventing the contamination of the windows by particles. This method is not usable in a photoacoustic measuring cell according to FIG. 2 for acoustical reasons: the rinsing air flow causes a "whistling" sound meaning that an essentially higher parasitic signal is superimposed over the desired measured signal.

It was the object of the present invention to provide a measuring cell that will reduce the soiling of the windows at the entry points of the radiation into the cell and that will slow down the deposition of the particles of the measured aerosol thereon in such a way that operation of the measuring cell is possible with a high level of sensitivity over long periods of time, while avoiding the above referred to disadvantages

SUMMARY OF THE INVENTION

To achieve this object, it is envisioned according to the invention that two flow entries are provided for at the ends of the tube section that are opposite each other, and at least one exit at a location that is centered between the entries. This way, the flow of the gas into the measuring cell is not directed from one side to the other. Instead, the gas is divided into two partial flows that are fed into the measuring cell between the windows and the resonant tube cell with the sensor microphone and a second cell section. The partial flows of the sample gas then flow in two partial cells against each other and exit the measuring cell via one or several exit channels that are arranged in proximity to the middle. By avoiding the "collision" of the gas flow with the windows and/or other entry points of the radiation, the particle deposition is considerably reduced at these locations.

According to an advantageous embodied example of the invention, the flow entries and/or the at least one flow exit transition into ring channels that are coaxially relative to the tube section. From these ring channels extend entry flow and/or exit flow channels radially to the tube section. Thereby it is possible to achieve a more even inflow to and outflow from the measuring cell. This way, the occurrence of turbulences is considerably reduced that might otherwise cause deposition of particles at the entry points of the radiation.

With the same effect, another embodied example of the measuring chamber according to the invention could envision that the flow is conducted through small ring slots from the entries and/or the at least one exit ring channels to the tube section.

Depending on the apparatus, the second partial cell may be realized as resonant or non-resonant.

An advantage is delivered by an embodied example of the invention, which contains a non-resonant second partial cell that is present in addition to the resonant measuring cell with the centered sensor microphone. In this embodiment one entry and a centered exit are arranged at the ends of the resonant partial cell, which is delimited by a chamber with a cross-sectional area that is expanded relative to the tube section ("middle chamber"); and following the chamber that is adjacent to the exit is another tube section with similarly large cross-sectional area as that of the resonant partial cell and another chamber with a cross-sectional area that is expanded relative to the tube section. The second entry is envisioned at the end of the further tube section that is arranged opposite to the exit. The second partial cell thereby is formed by the "middle chamber" that is expanded relative to the resonant tube section and the other tube section with similarly large cross-sectional area as that of the resonant partial cell. If the second partial cell were also embodied as a resonant cell adjacent to the measuring cell, then a reduction of the signal in the first partial cell would result. With the non-resonant second partial cell this is not the case.

In this variant, the length of the middle chamber and of the further tube section is preferably approximately half of the length of the tube section, respectively, of the resonant partial cell.

In order to be able to achieve an amplification of the signal in the first partial cell by also configuring the second partial cell as resonant, an embodied example is advantageously used in which are envisioned an entry and a first of two centered exits at the ends of a resonant partial cell, which is delimited by a chamber with a cross-sectional area that is expanded relative to the tube section, and whereby the chamber that is adjacent to the first exit is followed by a further tube section with similar cross-sectional area and length as that of the resonant partial cell, as well as another chamber with a cross-sectional area that is expanded relative to the tube section, and whereby a second centered exit is envisioned at the end of the further tube section that follows the centered chamber, and the second entry is envisioned at the end of the further tube section that is arranged opposite of the exit.

Preferably, the length of the middle chamber and of the further tube section is selected as being approximately the same length as that of the resonant partial cell.

The invention is illustrated in more detail in the description below using the enclosed drawings.

BRIEF DESCRIPTION OF THE DRAWINGS

FIG. 1 shows a schematic depiction of the principle of photo-acoustical measuring;

FIG. 2 shows the principal setup of a (longitudinally) resonant photo-acoustical measuring cell;

FIG. 3 shows a representation of the flow in the measuring cell according to FIG. 2;

FIG. 6 shows a depiction that is equivalent to FIG. 4 of the flow inside the measuring cell according to the invention.

DETAILED DESCRIPTION OF THE INVENTION

In general, the following rules must be followed for configuring the measuring cell, schematically depicted in the longitudinal section in FIG. 2, for photo-acoustical measurements according to the principle that is schematically depicted in FIG. 1:

The resonance frequency of the measuring cell resonance tube R with the microphone M that is axially penetrated by the laser beam L is determined primarily by the length of the tube. With approximately symmetrical reflective conditions at the tube ends, the standing acoustical pressure wave has its maximum approximately in the middle and two vibration nodes at the tube ends ("fixed" ends of the resonator). The length of the tube R is therefore approximately lambda/2, and the microphone M must be positioned approximately in the middle.

The windows form a fixed end for the sound particle velocity, which must therefore disappear there, while the sound pressure (which is phase shifted by lambda/2 relative to the sound particle velocity) reaches a maximum. Taking this condition and the effects explained in the paragraph before, the total length of the measuring cell amounts to approximately n·lambda/2, whereby n represents an integer number.

The entry and exit channels for the measured gas are preferably positioned in the pressure nodes of the sound wave. Then the interference, e.g. from turbulences, caused by the inflow of the measuring gas will only minimally influence the standing wave and the measured signal.

Deviations from the simple integer-number relation between the actual lengths of the partial cells and a lambda/4 (quarter of the wave length) are caused by the phase-shifting effect of the "notch" filter AN or, in other words, by the reflective and transmission conditions that exist at the transitions between sections of different diameters. If these transitions are possibly configured not sharply but with some smoothness, deviations from the ideal phase shift value of 180° can occur. This must be taken into consideration—either empirically or by suitable simulation calculations.

Figure 4:
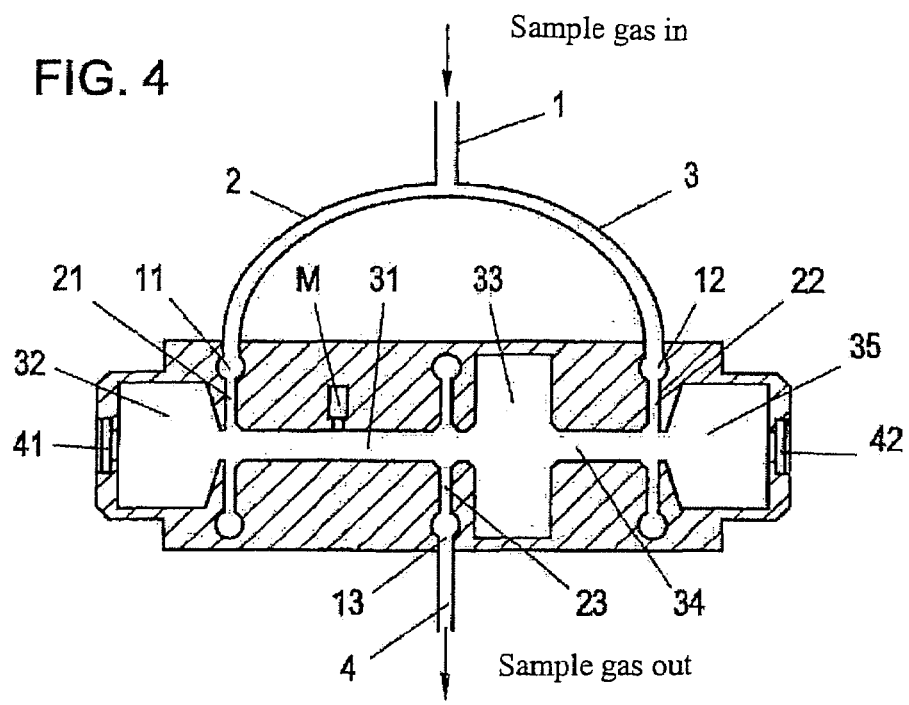
FIG. 4 shows a longitudinal section of a first embodied example of the measuring cell according to the invention with non-resonant second partial cell.

A first embodied example according to the invention is a measuring cell that is represented in an exemplary manner in a longitudinal section in FIG. 4. Here, the sample gas is introduced into the measuring cell via a sample gas line 1, divided via the separated entry lines 2 and 3 into two separate partial flows and guided from the entries 2, 3 to the ring channels 11 and 12 of the measuring cell. From there, the partial flows radially enter through ring slots 21 and 22 or through radial channels into the measuring tube 31 and into a coaxial tube 34 of similar dimensions; and the measuring tube 31 and the tube 34 are separated from each other by a chamber 33 with an expanded cross-sectional area. The partial flows of the sample gas, coming from the outward direction, flow through the partial cells 31 and 33, 34 to the middle of the cell. And from there, they flow through the ring slot 23 and the ring channel 13 into the exit line 4. During this process, the sample gas flows away from the outer chambers 32, 35 with larger cross-sectional areas and away from the windows 41 and 42 that are necessary for the transmission of the radiation. Transporting of the sample gas flow can be effected by way of a pump behind the measuring cell, not shown here, or, for example, by the exhaust pressure in the exhaust system of a combustion engine.

The period of irradiation must be harmonized via known methods with the resonance frequency of the cell. Then, if absorbing substances are present in the sample gas, the signal of the sensor microphone M in the "resonant" first partial cell with a resonance tube 31 of the length of approximately lambda/2 has the same frequency as the radiation and can therefore be detected with great sensitivity and selectivity by means that are known in the art (e.g. with the so-called "lock-in" technique and/or with a synchronous demodulator).

The second partial cell comprises the segments 33, 34 of different diameters and of lengths of approximately lambda/4, which is why no standing wave resonant with the period of irradiation can form in this partial cell, based on the underlying laws of physics. This fact is obvious to the expert in the field. The apparatus in FIG. 4 also necessarily requires that the second partial cell is non-resonant. In fact, a resonant standing wave in this partial cell would be displaced by lambda/2 or by the phase $\pi$ (=180°) relative to the standing wave in the first partial cell. The two standing waves would cancel each other out or weaken each other and one would obtain either no signal at all or only a minimal signal from the sensor microphone M of the measuring tube 31 of the "resonant" first partial cell.

Figure 5:
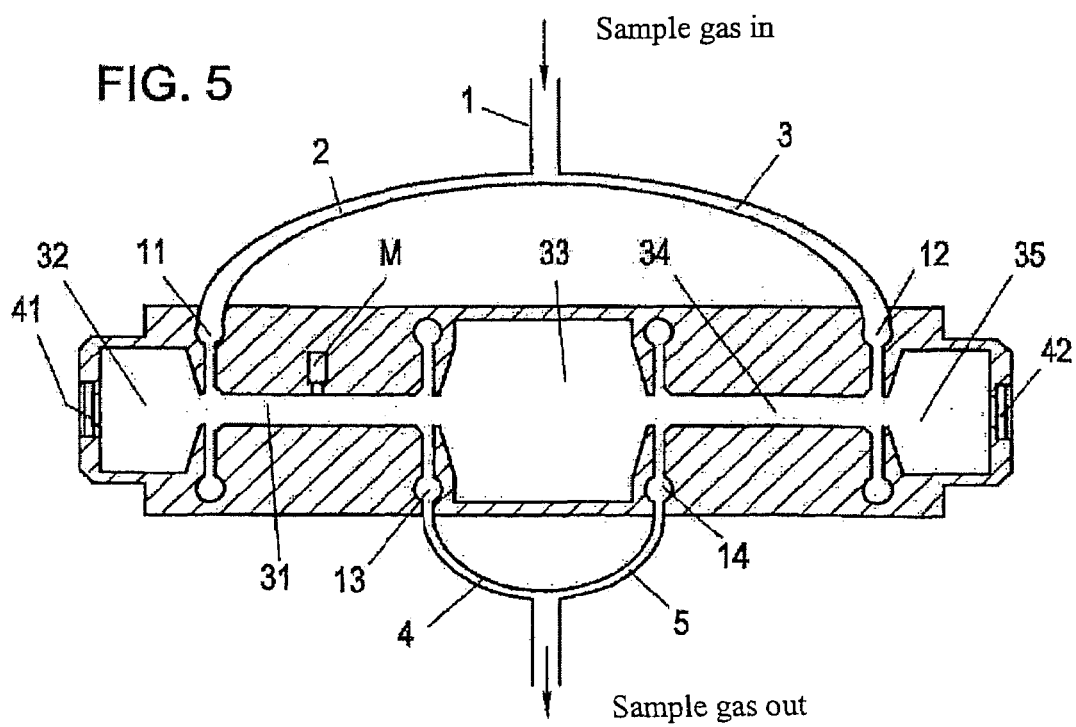
FIG. 5 shows a longitudinal section of another embodied example of the measuring cell according to the invention with resonant second partial cell.

In the embodied example of the measurement cell corresponding to FIG. 5, both partial cells can be realized as resonant. Due to the fact that a compensation space 33 with expanded diameter, that has a length of approximately lambda/2, is arranged between the two partial cell resonators 31 and 34, the phase shift between the standing waves of the first partial cells and of the second partial cell is approximately lambda, and the resulting phase shift is $2\pi$ (or 360°). The result is a constructive (positive) superposition of the waves, and the signal from sensor microphone M in measuring tube 31 of the "resonant" first partial cell is amplified. The disadvantage of this cell consists in the fact that its length is larger leading not only to an increase of the construction volume but also requiring better parallel focusing of the radiation in order to maintain a sufficiently small beam diameter across a larger length. A small beam diameter is absolutely critical because radiation must not reach the walls of the narrow long tubes 31, 34 in order to avoid interference signals.

The result of a finite element calculation of the flow in a cell in accordance with FIG. 4 is represented in FIG. 6. Here too, as for the FIG. 3 relating to the prior art, the direction and the velocity of the flow are characterized by the direction and the length of vectors. It is clearly evident that there occurs neither a direct nor a vortex flow toward the windows. On the experimental level too, it has been verified that with an embodiment according to the invention the windows 41, 42 of the measuring cell get soiled only slowly and comparatively minimally, thereby allowing for a long duration of the measurement without the need of cleaning the windows.

The invention claimed is:

1. Apparatus for use in photo-acoustical measurements of radiation-absorbing substances in samples comprising, a housing which defines a tubular measuring channel, entry and exit windows aligned with said tubular measuring channel to enable a laser beam to enter the housing through the entry window, pass through the tubular measuring channel and exit the housing through the exit window, a first expanded chamber between the entry window and a first end of the tubular measuring channel, said first chamber having a larger cross-sectional area than a cross-sectional area of the tubular measuring channel, a second expanded chamber between the exit window and a second end of the tubular measuring channel, the second chamber having a larger cross-sectional area than the cross-sectional area of the tubular measuring channel, a third expanded chamber along the tubular measuring channel between the first and second expanded chambers which has a larger cross-sectional area than a cross-sectional area of the tubular measuring channel, a microphone in communication with the tubular measuring channel, a first sample entry channel in communication with the tubular measuring channel near the first end thereof, a second sample entry channel in communication with the tubular measuring channel near the second end thereof, and a first sample discharge channel in communication with the tubular measuring channel at a location between said first and second sample entry channels.

2. Apparatus according to claim 1, wherein said first sample discharge channel is located about midway between the first and second entry channels.

3. Apparatus according to claim 2, wherein said microphone communicates with the tubular channel on one side of the first sample discharge channel and the third chamber is located on an opposite side of the first sample discharge channel.

4. Apparatus according to claim 1, wherein said housing defines a first ring channel radially outwardly of the tubular measuring channel near the first end thereof and a first ring slot which extends from the first ring channel to the tubular measuring channel.

5. Apparatus according to claim 4, wherein said housing defines a second ring channel radially outwardly of the tubular measuring channel near the second end thereof, and a second ring slot which extends from the second ring channel to the tubular measuring channel.

6. Apparatus according to claim 1, including a second sample discharge channel in communication with the tubular measuring channel between the first and second sample entry channels.

7. Apparatus according to claim 6, wherein said third chamber is centered along said tubular measuring channel, and said first and second sample discharge channels connect to said tubular measuring channel on opposite sides of said third chamber.

8. Apparatus according to claim 1, including a sample inlet line and separate first and second branch lines which respectively connect said sample inlet line to said first and second sample entry channels.

* * * * *